United States Patent
LV et al.

(10) Patent No.: US 8,993,810 B2
(45) Date of Patent: Mar. 31, 2015

(54) PREPARATION METHOD OF LYCOPENE INTERMEDIATE 3-METHYL-4,4-DIALKOXY-1-BUTALDEHYDE

(71) Applicants: Nanjing University of Technology, Nanjing (CN); Zhejiang Medicine Co., Ltd. Xinchang Pharmaceutical Factory, Donglu (CN)

(72) Inventors: Chunlei LV, Huancheng Donglu (CN); Shiqing Pi, Huancheng Donglu (CN); Jianhui Chen, Huancheng Donglu (CN); Dingqiang Lu, Huancheng Donglu (CN); Pingkai Ouyang, Huancheng Donglu (CN)

(73) Assignees: Nanjing University of Technology, Nanjing (CN); Zhejiang Medicine Co., Ltd. Xinchang Pharmaceutical Factory, Huancheng Donglu (CN)

( * ) Notice: Subject to any disclaimer, the term of this patent is extended or adjusted under 35 U.S.C. 154(b) by 0 days.

(21) Appl. No.: 14/369,137

(22) PCT Filed: Dec. 10, 2012

(86) PCT No.: PCT/CN2012/001667
§ 371 (c)(1),
(2) Date: Jun. 26, 2014

(87) PCT Pub. No.: WO2013/097285
PCT Pub. Date: Jul. 4, 2013

(65) Prior Publication Data
US 2014/0357900 A1  Dec. 4, 2014

(30) Foreign Application Priority Data

Dec. 26, 2011 (CN) .......................... 2011 1 0440217

(51) Int. Cl.
*C07C 45/00* (2006.01)
*C07C 45/30* (2006.01)
*C07C 41/22* (2006.01)

(52) U.S. Cl.
CPC ................. *C07C 45/30* (2013.01); *C07C 41/22* (2013.01)
USPC ........................................... 568/486; 568/488

(58) Field of Classification Search
USPC .................................................. 568/486, 488
See application file for complete search history.

(56) References Cited

U.S. PATENT DOCUMENTS 4,578,462 A * 3/1986 Hansen et al. ................ 544/177
4,675,451 A * 6/1987 Andrade et al. .............. 568/486

* cited by examiner

*Primary Examiner* — Sikarl Witherspoon
(74) *Attorney, Agent, or Firm* — William D. Hare, Esq.; McNeely Hare & War, LLP

(57) ABSTRACT

Disclosed is a preparation method of the lycopene intermediate 3-methyl-4,4-dialkoxy-1-butaldehyde. The preparation method comprises the following steps: (1) reacting 2-methyl-3,3-dialkoxy-1-halopropane with magnesium powder in the solvent of anhydrous tetrahydrofuran at a temperature of 45~65° C. to generate a mixture of Grignard reagents under the protection of an inert gas; and (2) adding N,N-disubstituted carboxamide to the mixture of Grignard reagents and reacting at a temperature of 10° C.~35° C. to obtain 3-methyl-4,4-dialkoxy-1-butaldehyde. The process route of the present invention is simple and direct, the operation is easy, the conditions are mild and the yield is good, and thus the invention has commercial value.

7 Claims, No Drawings

PREPARATION METHOD OF LYCOPENE INTERMEDIATE 3-METHYL-4,4-DIALKOXY-1-BUTALDEHYDE

CROSS-REFERENCE TO RELATED APPLICATIONS

This application is a national phase application of PCT/CN2012/001667, filed on Dec. 10, 2012, which claims priority to Chinese Application No. 201110440217.0 filed on Dec. 26, 2011.

FIELD OF THE INVENTION

The present invention relates to a pharmaceutical chemical intermediate, in particular, relates to a preparation method of lycopene intermediate 3-methyl-4,4-dialkoxy-1-butyraldehyde.

BACKGROUND OF THE INVENTION 3-methyl-4,4-dialkoxy-1-butyraldehyde as a pharmaceutical chemical intermediate has favorable application prospect. The molecular structure thereof is special and has two kinds of groups such as aldehyde and acetal, both of them are especially suitable for construction of a double bond system. Recently it has been reported from CN201010189861.0 by Runbo Shen, etc. that a new preparation method of lycopene by using 3-methyl-4,4-dialkoxy-1-butyraldehyde as a raw material is a typical example as a pharmaceutical intermediate, and it takes the advantages of simple process route, easy operation, low cost, and great commercial value.

At present it is less reported on synthesis method of 3-methyl-4,4-dialkoxy-1-butyraldehyde, and currently there are mainly two methods:

A: 2-methyl-propylene dimethyl acetal (3) as a raw material, condenses with hydrogen and carbon monoxide to obtain the product (1) in the presence of catalyst and high pressure, the reaction equation is described as follows:

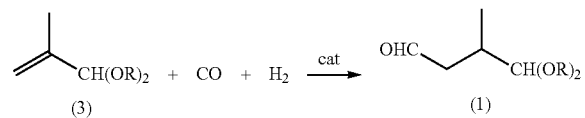

B: It was reported by Schmid etc. that 2-methyl-4-(N,N-diethyl)-2-butylene dimethyl acetal (4) as a raw material, rearranges to 2-methyl-4-(N,N-diethyl)-3-butylene dimethyl acetal (5) in the presence of catalyst of ruthenium and phosphorus complexes, and then hydrolyzes to obtain 3-methyl-4,4-dimethoxy-1-butyraldehyde (1A). The reaction equation is described as follows:

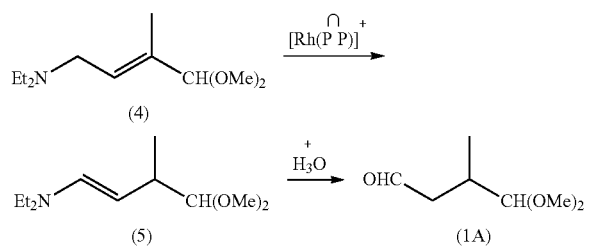

Both of the two process routes are simple, but it requires using hydrogen and carbon monoxide in the presence of catalyst and high pressure in the method A. It results in production equipments bringing about difficult and dangerous synthesis; 2-methyl-4-(N,N-diethyl)-2-butylene dimethyl acetal (4) of method B as a raw material is difficult to acquire and synthesize; and some expensive and complicated catalysts are used in the two processes. Both of these makes industrialization difficult.

SUMMARY OF THE INVENTION

The technical problem solved by the present invention is to overcome the above deficiencies of the prior art, and provide a preparation method of 3-methyl-4,4-dialkoxy-1-butyraldehyde in which the process route is simple and the raw material is easily available.

The preparation method of the present invention comprises the following steps: Step (1): reacting 2-methyl-3,3-dialkoxy-1-halopropane of Formula (2) with magnesium powder in a solvent of anhydrous tetrahydrofuran at a temperature of 45~65° C. (the temperature of Grignard reaction) to generate a mixture of Grignard reagent under the protection of an inert gas; and Step (2): adding N,N-disubstituted carboxamide to the mixture of Grignard reagent and reacting at a temperature of 10° C.~35° C. (the temperature of condensation reaction and hydrolysis reaction) to obtain 3-methyl-4,4-dialkoxy-1-butaldehyde of Formula (1). The reaction equation is described as follows:

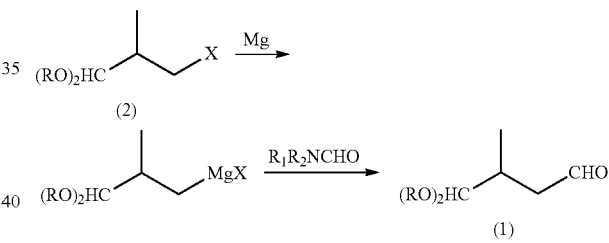

Wherein R is alkyl, preferably methyl or ethyl. The 2-methyl-3,3-dialkoxy-1-halopropane is 2-methyl-3,3-dimethoxy-1-chloropropane, 2-methyl-3,3-dimethoxy-1-bromopropane, 2-methyl-3,3-diethoxy-1-chloropropane, and 2-methyl-3,3-diethoxy-1-bromopropane. The N,N-disubstituted carboxamide is N,N-dimethyl formamide or N-formyl piperidine.

In the above reaction, preferably, a molar ratio of 2-methyl-3,3-dialkoxy-1-halopropane of Formula (2) to the magnesium powder is 1:1.0~1.5; preferably, a molar ratio of 2-methyl-3,3-dialkoxy-1-halopropane of Formula (2) to N,N-disubstituted carboxamide is 1:1.0~1.5. In addition, iodine may be added into the reactant of step (1) as an initiator of Grignard reaction.

The process route of the present invention is simple and direct, the operation is easy, the conditions are mild and the yield is good, and thus the invention has commercial value.

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Apparatuses and devices of the examples of the present invention are as follows: Gas chromatograph-Mass Spectrometer, MS5973N-GC6890N (Agilent Technologies, US); Nuclear Magnetic Resonance Spectrometer, AVANCE DMX 400M (TMS as internal standard, Bruker Corporation); Infrared Spectrometer, NICOLET 360FT-IR; Gas Chromatograph, Ke Xiao GC1690.

Example 1

Preparation of 3-methyl-4,4-dimethoxy-1-butyraldehyde 14.4 g (0.6 mol) magnesium powder, 300 ml anhydrous tetrahydrofuran and 10 mg iodine are added in 1 L four necked bottle under stirring and refluxing with protection of nitrogen, 2 ml of a solution containing 98 g (0.5 mol) 2-methyl-3,3-dimethoxy-1-bromopropane and 100 ml anhydrous tetrahydrofuran is added, and then mildly heated to initiate it and the reaction is initiated when the color of iodine disappears. Then the residual 2-methyl-3,3-dimethoxy-1-bromopropane is dropped at temperature of 45° C. for 1 hr, and reacted at 55° C. for 5 hr after finishing the dropping. Then the mixture is cooled to 30° C., and a solution of 67.8 g (0.6 mol) of N-formylpiperidine and 100 ml of anhydrous tetrahydrofuran is dropped for 0.5 hr, and continuously stirred for 0.5 hr after finishing the dropping. Then 100 ml of 10% ammonium chloride aqueous solution is added under stirring for 0.5 hr to separate a water layer. The organic layer is extracted with 600 ml of ether for 3 times. The combined organic layer is in turn washed by 100 ml of water, 100 ml of saturated sodium carbonate, and 100 ml of 10% sodium chloride aqueous solution, and dried by magnesium sulfate, filtrated, solvent is evaporated under a reduced pressure to dryness, to obtain 64.5 g crude product of 3-methyl-4,4-dimethoxy-1-butyraldehyde, 56.2 g fraction is collected at 65-68° C./3 mmHg under a reduced pressure, to obtain a colorless liquid, the content determined by gas chromatography is 98.2%, the yield is 76.3%.

Determination of Product Structure $^1$HNMR (δ, ppm, 400 MHz, DMSO): 0.875 (d, J=6.8 Hz, 3H, CH$_3$); 2.173-2.459 (m, 2H, CH*$_2$CHO); 2.274-2.339 (m, 1H, CH*CH$_3$); 3.268 (s, 6H, OCH$_3$); 4.098 (d, J=6.0 Hz, 1H, CH*(OCH$_3$)$_2$); 9.598 (t, J=2.0 Hz, 1H, CHO);
$^{13}$CNMR (δ, ppm, 400 MHz, DMSO): 15.667, 31.569, 40.639, 54.151, 55.237, 108.137, 203.057
GC-MS: 29, 41, 47, 55, 75 (100%), 83, 85, 102, 115, 145
IR: 1067.99, 1101.36, 1723.71, 2832.36, 2937.00

Example 2

Preparation of 3-methyl-4,4-diethoxy-1-butyraldehyde 16.8 g (0.7 mol) magnesium powder, 300 ml anhydrous tetrahydrofuran and 10 mg iodine are added in 1 L four necked bottle under stirring and refluxing with protection of nitrogen, 2 ml of a solution containing 98 g (0.5 mol) 2-methyl-3,3-diethoxy-1-chloropropane and 100 ml anhydrous tetrahydrofuran is added, and then mildly heated to initiate it and the reaction is initiated when the color of iodine disappears. Then the residual 2-methyl-3,3-3,3-diethoxy-1-chloropropane is dropped at temperature of 65° C. for 1 hr, and reacted at 65° C. for 8 hr after finishing the dropping. Then the mixture is cooled to 30° C., and a solution of 40.2 g (0.55 mol) DMF and 50 ml of anhydrous tetrahydrofuran is dropped for 0.5 hr, and continuously stirred for 0.5 hr after finishing the dropping. Then 100 ml of 10% ammonium chloride aqueous solution is added under stirring for 0.5 hr to separate a water layer. The organic layer is extracted with 600 ml of ether for 3 times. The combined organic layer is in turn washed by 100 ml of water, 100 ml of saturated sodium carbonate, and 100 ml of 10% sodium chloride aqueous solution, and dried by magnesium sulfate, filtrated, solvent is evaporated under a reduced pressure to dryness, to obtain 114.6 g crude product of 3-methyl-4,4-diethoxy-1-butyraldehyde, 107.2 g fraction is collected at 72-75° C./3 mmHg under a reduced pressure, to obtain a colorless liquid, the content determined by gas chromatography is 98.6%, the yield is 61.6%.

Determination of Product Structure $^1$HNMR (δ, ppm, 400 MHz, CDCl$_3$): 1.000 (d, J=5.6 Hz, 3H, CH$_3$); 1.206 (d, J=7.2 Hz, 6H, OCH$_2$CH*$_3$); 2.222-2.588 (m, 2H, CH*$_2$CHO); 2.360-2.425 (m, 1H, CH*CH$_3$); 2.634-3.750 (m, 4H, OCH*$_2$CH$_3$)); 4.220 (d, J=6.0 Hz, 1H, CH*(OCH$_2$CH$_3$)$_2$); 9.735 (t, J=2.4 Hz, 1H, CHO);
$^{13}$CNMR (δ, ppm, 400 MHz, CDCl$_3$): 14.932, 15.103, 15.419, 32.372, 46.188, 61.945, 63.327, 106.010, 201.766
GC-MS: 29, 43, 47, 55, 75, 83, 86, 101, 103 (100%), 129, 173
IR: 1051.73, 1071.02, 1738.70, 2831.38, 2937.62

Examples 3-8

Preparation of 3-methyl-4,4-dimethoxy-1-butyraldehyde

Some amount of magnesium powder, 100 ml anhydrous tetrahydrofuran and 10 mg iodine are added in 500 L four necked bottle under stirring and refluxing with protection of nitrogen, 2 ml of a solution containing 0.1 mol 2-methyl-3,3-dimethoxy-1-halopropane and 20 ml anhydrous tetrahydrofuran is added, and then mildly heated to initiate it and the reaction is initiated when the color of iodine disappears. Then the residual 2-methyl-3,3-dimethoxy-1-halopropane is dropped at some temperature for 0.5 hr, and reacted at the temperature for 5 hr after finishing the dropping. Then the mixture is cooled to 30° C., and a solution of some amount of N,N-disubstituted carboxamide and 20 mL of anhydrous tetrahydrofuran is dropped for 0.5 hr, and continuously stirred for 0.5 hr after finishing the dropping. Then 30 mL of 10% ammonium chloride aqueous solution is added under stirring for 0.5 hr to separate a water layer. The organic layer is extracted with 150 mL of ether for 3 times. The combined organic layer is in turn washed by 30 mL of water, 30 mL of saturated sodium carbonate, and 30 mL of 10% sodium chloride aqueous solution, and dried by magnesium sulfate, filtrated, solvent is evaporated under a reduced pressure to dryness, to obtain crude product of 3-methyl-4,4-dimethoxy-1-butyraldehyde, fraction is collected at 65-68° C./3 mmHg under a reduced pressure, to obtain a colorless liquid, to calculate the content determined by gas chromatography, the yield. The results are shown in Table 1.

Determination of Product Structure of Examples 3-8 is the Same as Example 1

$^1$HNMR (δ, ppm, 400 MHz, DMSO): 0.875 (d, J=6.8 Hz, 3H, CH$_3$); 2.173-2.459 (m, 2H, CH*$_2$CHO); 2.274-2.339 (m, 1H, CH*CH$_3$); 3.268 (s, 6H, OCH$_3$); 4.098 (d, J=6.0 Hz, 1H, CH*(OCH$_3$)$_2$); 9.598 (t, J=2.0 Hz, 1H, CHO);
$^{13}$CNMR (δ, ppm, 400 MHz, DMSO): 15.667, 31.569, 40.639, 54.151, 55.237, 108.137, 203.057
GC-MS: 29, 41, 47, 55, 75 (100%), 83, 85, 102, 115, 145
IR: 1067.99, 1101.36, 1723.71, 2832.36, 2937.00

TABLE 1

Reactants, Reaction temperatures and Results of Examples 3-8

| Example No | 2-methyl-3,3-dimethoxy-1-halopropane | Dosage of Mg power (mole) | Temperature of Grignard reaction (°C.) | Categories of N,N-disubstituted carboxamide and dosage (mole) | Temperature of condensation reaction (°C.) | Weight of product (g) | Content of gas Phase (%) | yield (%) |
|---|---|---|---|---|---|---|---|---|
| 3 | 2-methyl-3,3-dimethoxy-1-chloropropane | 0.15 | 65 | N,N-dimethyl formamide, 0.11 | 25 | 9.4 | 94.2 | 63.7 |
| 4 | 2-methyl-3,3-dimethoxy-1-chloropropane | 0.13 | 60 | N-formylpiperidine 0.13 | 30 | 8.8 | 94.9 | 60.2 |
| 5 | 2-methyl-3,3-dimethoxy-1-bromopropane | 0.11 | 55 | N,N-dimethyl formamide, 0.14 | 20 | 10.4 | 95.2 | 71.2 |
| 6 | 2-methyl-3,3-dimethoxy-1-bromopropane | 0.10 | 50 | N-formylpiperidine 0.12 | 15 | 10.7 | 93.7 | 73.3 |
| 7 | 2-methyl-3,3-dimethoxy-1-chloropropane | 0.12 | 50 | N,N-dimethyl formamide, 0.15 | 10 | 8.4 | 94.0 | 57.7 |
| 8 | 2-methyl-3,3-dimethoxy-1-bromopropane | 0.14 | 45 | N-formylpiperidine, 0.10 | 35 | 9.9 | 95.3 | 69.0 |

Examples 9-14

Preparation of 3-methyl-4,4-diethoxy-1-butyraldehyde

Some amount of magnesium powder, 100 ml anhydrous tetrahydrofuran and 10 mg iodine are added in 500 L four necked bottle under stirring and refluxing with protection of nitrogen, 2 ml of a solution containing 0.1 mol 2-methyl-3,3-diethoxy-1-halopropane and 20 ml anhydrous tetrahydrofuran is added, and then mildly heated to initiate it and the reaction is initiated when the color of iodine disappears. Then the residual 2-methyl-3,3-diethoxy-1-halopropane is dropped at some temperature for 0.5 hr, and reacted at the temperature for 5 hr after finishing the dropping. Then the mixture is cooled to 30° C., and a solution of some amount of N,N-disubstituted carboxamide and 20 mL of anhydrous tetrahydrofuran is dropped for 0.5 hr, and continuously stirred for 0.5 hr after finishing the dropping. Then 30 mL of 10% ammonium chloride aqueous solution is added under stirring for 0.5 hr to separate a water layer. The organic layer is extracted with 150 mL of ether for 3 times. The combined organic layer is in turn washed by 30 mL of water, 30 mL of saturated sodium carbonate, and 30 mL of 10% sodium chloride aqueous solution, and dried by magnesium sulfate, filtrated, solvent is evaporated under a reduced pressure to dryness, to obtain crude product of 3-methyl-4,4-diethoxy-1-butyraldehyde, fraction is collected at 72-75° C./3 mmHg under a reduced pressure, to obtain a colorless liquid, to calculate the content determined by gas chromatography, the yield. The results are shown in Table 2.

Determination of Product Structure of Examples 9-14 is the Same as Example 2

$^1$HNMR (δ, ppm, 400 MHz, CDCl$_3$): 1.000 (d, J=5.6 Hz, 3H, CH$_3$); 1.206 (d, J=7.2 Hz, 6H, OCH$_2$CH*$_3$); 2.222-2.588 (m, 2H, CH*$_2$CHO); 2.360-2.425 (m, 1H, CH*CH$_3$); 2.634-3.750 (m, 4H, OCH*$_2$CH$_3$)); 4.220 (d, J=6.0 Hz, 1H, CH* (OCH$_2$CH$_3$)$_2$); 9.735 (t, J=2.4 Hz, 1H, CHO);

$^{13}$CNMR (δ, ppm, 400 MHz, CDCl$_3$): 14.932, 15.103, 15.419, 32.372, 46.188, 61.945, 63.327, 106.010, 201.766

GC-MS: 29, 43, 47, 55, 75, 83, 86, 101, 103 (100%), 129, 173

IR: 1051.73, 1071.02, 1738.70, 2831.38, 2937.62

TABLE 2

Reactants, Reaction temperatures and Results in Examples 9-14

| Example No | 2-methyl-3,3-diethoxy-1-halopropane | Dosage of Mg power (mole) | Temperature of Grignard reaction (°C.) | Categories of N,N-disubstituted carboxamide and dosage (mole) | Temperature of condensation reaction (°C.) | Weight of product (g) | Content of gas phase (%) | Yield (%) |
|---|---|---|---|---|---|---|---|---|
| 9 | 2-methyl-3,3-diethoxy-1-chloropropane | 0.11 | 65 | N,N-dimethyl formamide, 0.14 | 15 | 11.1 | 96.2 | 63.8 |
| 10 | 2-methyl-3,3-diethoxy-1-chloropropane | 0.12 | 60 | N-formylpiperidine, 0.13 | 20 | 10.8 | 95.7 | 62.1 |
| 11 | 2-methyl-3,3-diethoxy-1-bromopropane | 0.13 | 55 | N,N-dimethyl formamide, 0.11 | 30 | 13.2 | 94.2 | 74.2 |
| 12 | 2-methyl-3,3-diethoxy-1-bromopropane | 0.14 | 50 | N-formylpiperidine, 0.12 | 35 | 12.2 | 95.1 | 70.1 |

TABLE 2-continued

Reactants, Reaction temperatures and Results in Examples 9-14

| Example No | 2-methyl-3,3-diethoxy-1-halopropane | Dosage of Mg power (mole) | Temperature of Grignard reaction (° C.) | Categories of N,N-disubstituted carboxamide and dosage (mole) | Temperature of condensation reaction (° C.) | Weight of product (g) | Content of gas phase (%) | Yield (%) |
|---|---|---|---|---|---|---|---|---|
| 13 | 2-methyl-3,3-diethoxy-1-chloropropane | 0.15 | 55 | N-formylpiperidine, 0.15 | 25 | 11.3 | 95.5 | 65.2 |
| 14 | 2-methyl-3,3-diethoxy-1-bromopropane | 0.10 | 45 | N,N-dimethyl formamide, 0.10 | 10 | 12.5 | 94.8 | 71.6 |

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. A preparation method of lycopene intermediate 3-methyl-4,4-dialkoxy-1-butyraldehyde, comprising the following steps:

Step (1): reacting 2-methyl-3,3-dialkoxy-1-halopropane of Formula (2) with magnesium powder in a solvent of anhydrous tetrahydrofuran at a temperature of 45~65° C. to generate a mixture of Grignard reagent under the protection of an inert gas; and Step (2): adding N,N-disubstituted carboxamide to the mixture of Grignard reagent and reacting at a temperature of 10° C.~35° C. to obtain 3-methyl-4,4-dialkoxy-1-butaldehyde of Formula (1), its reaction equation is described as follows:

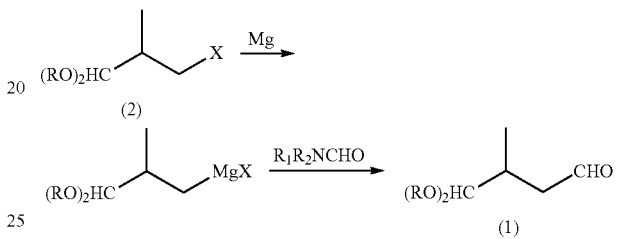

wherein R is alkyl.

2. The preparation method according to claim 1, wherein the alkyl is methyl or ethyl.

3. The preparation method according to claim 1, wherein the 2-methyl-3,3-dialkoxy-1-halopropane is 2-methyl-3,3-dimethoxy-1-chloropropane, 2-methyl-3,3-dimethoxy-1-bromopropane, 2-methyl-3,3-diethoxy-1-chloropropane, and 2-methyl-3,3-diethoxy-1-bromopropane.

4. The preparation method according to claim 1, wherein the N,N-disubstituted carboxamide is N, N-dimethyl formamide or N-formyl piperidine.

5. The preparation method according to claim 1, wherein a molar ratio of 2-methyl-3,3-dialkoxy-1-halopropane to the magnesium powder is 1:1.0~1.5.

6. The preparation method according to claim 1, wherein a molar ratio of 2-methyl-3,3-dialkoxy-1-halopropane to N,N-disubstituted carboxamide is 1:1.0~1.5.

7. The preparation method according to claim 1, wherein, the reactants of step (1) further comprise iodine.

* * * * *